US009116131B2

(12) United States Patent
Jurca

(10) Patent No.: US 9,116,131 B2
(45) Date of Patent: Aug. 25, 2015

(54) METHOD AND MONITORING DEVICE FOR THE DETECTION AND MONITORING OF THE CONTAMINATION OF AN OPTICAL COMPONENT IN A DEVICE FOR LASER MATERIAL PROCESSING

(71) Applicant: Marius Jurca, Stattmatten (FR)

(72) Inventor: Marius Jurca, Stattmatten (FR)

( * ) Notice: Subject to any disclaimer, the term of this patent is extended or adjusted under 35 U.S.C. 154(b) by 0 days.

(21) Appl. No.: 13/804,177

(22) Filed: Mar. 14, 2013

(65) Prior Publication Data
US 2013/0258321 A1 Oct. 3, 2013

(30) Foreign Application Priority Data

Mar. 30, 2012 (DE) .......................... 10 2012 102 785

(51) Int. Cl.
| | | |
|---|---|---|
| *G01N 21/00* | (2006.01) | |
| *G01N 21/95* | (2006.01) | |
| *G01M 11/00* | (2006.01) | |
| *G01M 11/02* | (2006.01) | |
| *G01N 21/94* | (2006.01) | |
| *G01N 21/958* | (2006.01) | |
| *B23K 26/30* | (2014.01) | |

(52) U.S. Cl.
CPC .............. *G01N 21/95* (2013.01); *B23K 26/428* (2013.01); *G01M 11/005* (2013.01); *G01M 11/0278* (2013.01); *G01N 21/94* (2013.01); *G01N 21/958* (2013.01)

(58) Field of Classification Search
CPC .............. G01N 21/958; G01N 21/896; G01N 2021/9586; G01N 21/8803; G01M 11/00
USPC ..................... 356/239.1; 250/459.1; 345/167; 362/282
See application file for complete search history.

(56) References Cited

U.S. PATENT DOCUMENTS

| | | | | |
|---|---|---|---|---|
| 5,991,480 | A * | 11/1999 | Kunz et al. ...................... 385/37 |
| 6,088,092 | A * | 7/2000 | Chen et al. .................. 356/237.2 |
| 6,118,527 | A | 9/2000 | Jurca |
| 6,281,500 | B1 * | 8/2001 | Gaon .......................... 250/339.1 |
| 6,836,202 | B1 | 12/2004 | Kim |
| 7,023,538 | B2 | 4/2006 | Hutt et al. |
| 7,193,700 | B2 | 3/2007 | Fliss |
| 2004/0008342 | A1 | 1/2004 | Hutt et al. |
| 2004/0114134 | A1 | 6/2004 | Fliss |
| 2004/0174797 | A1 * | 9/2004 | Tsukagoshi ................... 369/103 |
| 2006/0043077 | A1 | 3/2006 | Nittner |
| 2009/0015559 | A1 * | 1/2009 | Day et al. ...................... 345/167 |

(Continued)

FOREIGN PATENT DOCUMENTS

| | | | |
|---|---|---|---|
| BE | 1007005 A3 | 2/1995 | |
| DE | 19507401 A1 | 10/1995 | |

(Continued)

*Primary Examiner* — Tarifur Chowdhury
*Assistant Examiner* — Md Rahman
(74) *Attorney, Agent, or Firm* — Fleit Gibbons Gutman Bongini & Bianco PL; Martin Fleit; Paul D. Bianco

(57) ABSTRACT

A method and device for the detection and monitoring of the contamination of an optical component in a device for laser material processing, which emits a process laser beam through or onto the optical component. A measurement beam emitted by a light source is projected under an angle of incidence onto an optical surface of the optical component. The beam reflected from the outer surface of the protective window under the angle of reflection corresponding to the angle of incidence is conducted through an aperture stop onto a first light-sensitive detector so as to record the intensity of the reflected beam. The intensity of the scattered radiation, scattered diffusely from the optical surface of the component under a scattering angle, is recorded by a second light-sensitive detector. The degree of the contamination of the component is determined from the recorded intensities of the reflected beam and the scattered radiation.

20 Claims, 5 Drawing Sheets

(56) References Cited

U.S. PATENT DOCUMENTS

| | | | |
|---|---|---|---|
| 2009/0323051 A1* | 12/2009 | Matsui | 356/237.3 |
| 2010/0329697 A1* | 12/2010 | Koizumi et al. | 398/208 |
| 2011/0096646 A1* | 4/2011 | Rutschmann et al. | 369/44.23 |
| 2011/0194288 A1* | 8/2011 | Hsu | 362/282 |
| 2011/0226962 A1* | 9/2011 | Boudreau et al. | 250/459.1 |

FOREIGN PATENT DOCUMENTS

| | | | | |
|---|---|---|---|---|
| DE | 19605018 A1 | | 8/1997 | |
| DE | 19654850 A1 | | 7/1998 | |
| DE | 19839930 C1 | | 9/1999 | |
| DE | 10113518 A1 | | 10/2002 | |
| DE | 20314918 U1 | | 2/2005 | |
| DE | 10 2004 011 682 | | 3/2005 | |
| DE | 102004041682 A1 | | 3/2005 | |
| DE | 10 2004 041 682 | | 3/2006 | |
| EP | 1354664 A1 | | 10/2003 | |
| EP | 1398612 A1 | | 3/2004 | |
| EP | 1452851 | * | 9/2004 | G01N 21/15 |
| EP | 1488882 A1 | | 12/2004 | |
| WO | 9833059 A1 | | 7/1998 | |

* cited by examiner

METHOD AND MONITORING DEVICE FOR THE DETECTION AND MONITORING OF THE CONTAMINATION OF AN OPTICAL COMPONENT IN A DEVICE FOR LASER MATERIAL PROCESSING

CROSS REFERENCE TO RELATED APPLICATIONS

This application claims priority under 35 U.S.C. §119 to German Patent Application No. 10 2012 102 785.4 filed 30 Mar. 2012, the entire contents of which are incorporated herein by reference.

FIELD OF THE INVENTION

The invention concerns a method and a monitoring device for the detecting and monitoring of the contamination of an optical component, such as a lens, a protective window or a mirror, in a device for laser material processing.

BACKGROUND OF THE INVENTION

The use of optical components in the industrial environment primarily requires intact and clean optical surfaces of these components. In particular in beam shaping and deflection of high-power laser beams, the important thing is to always test the characteristics of the optical components used, such as lenses and mirrors, in the context of their functionality, since the high laser beam power density on the optical surfaces of the components can quickly lead to contamination, destruction, and to consequential damage. Particularly critical are applications in the area of laser material processing, in which, as a result of the spatial proximity of the processing head of the material processing device to the workpiece to be processed, one must reckon with an increased contamination, for example, due to fumes and material spatters produced by the process.

In order to minimize the costs of the unavoidable contamination of the optical components, protective devices, such as cross jet and antireflective (AR)-coated protective screens, are foreseen, with which the functional optical components such as lenses and mirrors are protected from contamination. In this application, the main thing is the functionality of the aforementioned AR-coated protective windows.

Frequently, the contamination in a device for laser material processing, such as laser welding or laser cutting, arises in the following manner: Liquid metal spatters from the laser induced molten metal pool, reach the (process-side) surfaces of the optical component of the device, facing the processing point (TCP, tool center point). Some spatters adhere to the process-side surface of the optical component and are immediately burned into the surface by the high beam power density of the process laser beam. In this way, the transmissivity of the optical components is reduced in proportion to the surface of the burned-in spatters. At the same time, the burned-in spatters absorb the laser output, so that the optical components, which are not very good thermal conductors, are heated on one side (process side). Consequently, the optical component can sustain damage or even burst as a result of thermal stresses. In particular, there may be a deformation due to the heating of the optical components, which can have a negative influence on the position of the focal point of the process laser beam in the TCP, so that aside from the output loss due to the burned-in spatters, an additional damage of the process quality may occur.

From the state of the art, devices for the detection and monitoring of the contamination of optical components and, in particular, protective windows in order to avoid these effects in devices for laser material processing are known.

Passive monitoring methods use the detection of scattered radiation of the process laser beam that is scattered by the spatters formed, as in the case of the publications DE19605018-A1, DE19507401-A1, WO9833059-A1, DE19839930-C1, DE10113518-A1, and EP1488882-A1. This can be carried out, for example, with a protective window, on- or off-axis above the protective window (on the side of the protective window turned away from the process), or laterally, by the measurement of the scattered radiation, coupled into the protective window. The known methods, however, have considerable disadvantages, which greatly limit a practical application. For example, a desired change of the output power of the process laser leads to false alarm signals (with an increase in output) or to a loss of the monitoring function (with a diminution of the output, since the relatively small increase of the useful monitoring signal can lay under the alarm threshold). The influence of the radiation of the process laser, reflected from the workpiece, is also uncontrolled. Furthermore, this kind of device is not free of disturbances ("fail-safe") in its mode of functioning, since in case of a breakage of the monitoring protective window or the not mounted or not properly mounted protective window, nothing can be measured.

Another known monitoring possibility is based on the measurement of the temperature of the protective window via contact temperature sensors. This takes place under the assumption that the burned-in spatters on the surface of the protective window lead to an increased absorption of the laser power and thus to a heating of the protective window. However, it has become evident that these known methods react in a very slow, not very sensitive manner and moreover, are dependent on the momentary value of the output power of the process laser and the laser power reflected from the surface of the protective window. Furthermore, these known methods are also not very free of disturbances in their mode of functioning since, in the case of a breakage of the monitored protective window or a not mounted or not properly mounted protective window, nothing can be measured.

A variant of the aforementioned passive monitoring possibilities provides for a measurement of the heat radiation of the burned-in contamination. It has become evident, however, that these methods are also dependent on the momentary value of the output power of the process laser and the laser power reflected from the surface of the protective window. Furthermore, this method is also not free from disturbances in its mode of functioning since, in the case of a breakage of the monitored protective window or a not mounted or not properly mounted protective window, nothing can be measured.

The active monitoring devices known from the state of the art, such as DE19839930-C1, DE20314918-A1, BE1007005-A1, EP01398612-A1, and DE19654850-A1, use additional light sources (for example, LEDs or laser diodes), in order to detect certain features of the protective window. Usually, several additional light sources are used with different functions, so as to guarantee a comprehensive monitoring. Thus, for example, a breakage of the protective window can be reliably detected. Alternatively, the active methods are also supplemented by passive measurement methods, which, however, have the disadvantages already indicated above and, moreover, increase the complexity of the monitoring device.

An active monitoring device known from BE 1007005-A1 and EP 01398612-A1 uses a type of reflected light barrier.

With this monitoring device, both the contamination as well as a breakage of the protective window can be, advantageously, quickly detected and this can be largely done independent of the laser output power of the process laser. Here also, the proposed solution is not optimal, since the sensitivity of the method is very low and greatly dependent on the optical characteristics of the scanned surface of the protective window. Furthermore, the measurement is also greatly dependent on the output power of an additional light source that emits a measurement beam onto the surface of the protective window.

A detection and monitoring method for the contamination of an optical component is known from EP 1354664-A1, where a measurement beam from a light source is projected under an incidence angle onto the outer surface of the optical component. Here in a first example of the set-up a light sensitive detector measures the scattered light from the outer surface of the optical component. In a second example of the set-up a detector measures the intensity of a beam, which is reflected from the outer surface of the optical component.

Another method for the detection and monitoring of the contamination of an optical component is known from DE 10 2004 041682-A1. Here the measurement radiation of a light source is projected onto a surface of an optical component under an incidence angle and the reflected and scattered radiation from the surface of the optical component is measured with a light-sensitive detector.

SUMMARY OF THE INVENTION

The goal of embodiments of the invention under consideration is to propose a method and a monitoring device to detect and monitor the contamination of an optical component in a device for laser material processing, with which the degree of contamination can be continuously detected reliably, quickly, and independent of output fluctuations of the process laser beam and independent of the characteristics of the surface of the component to be monitored during the ongoing material processing. Furthermore, with the method and the device, it should also become possible to ascertain a breakage of the optical component to be monitored or to determine that the optical component is missing.

In the method in accordance with the invention for the detection and monitoring of the contamination of an optical component, the following steps are carried out:
- a measurement beam emitted from a light source is projected under an angle of incidence onto an outer surface of the optical component;
- the beam reflected from the outer surface of the optical component under the angle of reflection corresponding to the angle of incidence is conducted by an aperture stop onto a first light-sensitive detector in order to record the intensity of the reflected beam;
- the diffusive intensity of the scattered beam from the outer surface of the optical component is conducted under a scattering angle onto a second light-sensitive detector in order to record the intensity of the scattered beam;
- and the degree of the contamination of the optical component is finally determined from the recorded intensities of the reflected beam and the scattered radiation.

The monitoring device in accordance with the invention for the detecting and monitoring of the contamination of an optical component in a device for laser material processing, which emits a process laser beam through or onto the optical component, comprises the following components:
- a light source that emits a measurement beam and projects it under an angle of incidence onto an optical surface of the optical component;
- a first light-sensitive detector;
- an aperture stop through which the beam reflected from the optical surface of the optical component under the angle of reflection is conducted onto the first detector so as to record the intensity of the reflected beam;
- a second light-sensitive detector that records the intensity of the scattered radiation, diffusely scattered from the optical surface of the optical component under a scattering angle;
- and an evaluation device that determines a measure for the degree of the contamination of the optical component from the recorded intensities of the reflected beam and the scattered radiation.

BRIEF DESCRIPTION OF THE DRAWINGS

An embodiment example of the invention, in which the contamination of a protective window in a device for laser material processing is detected and monitored, is explained in more detail below, with reference to the appended drawings. The drawings show the following.

DETAILED DESCRIPTION

Figure 1:
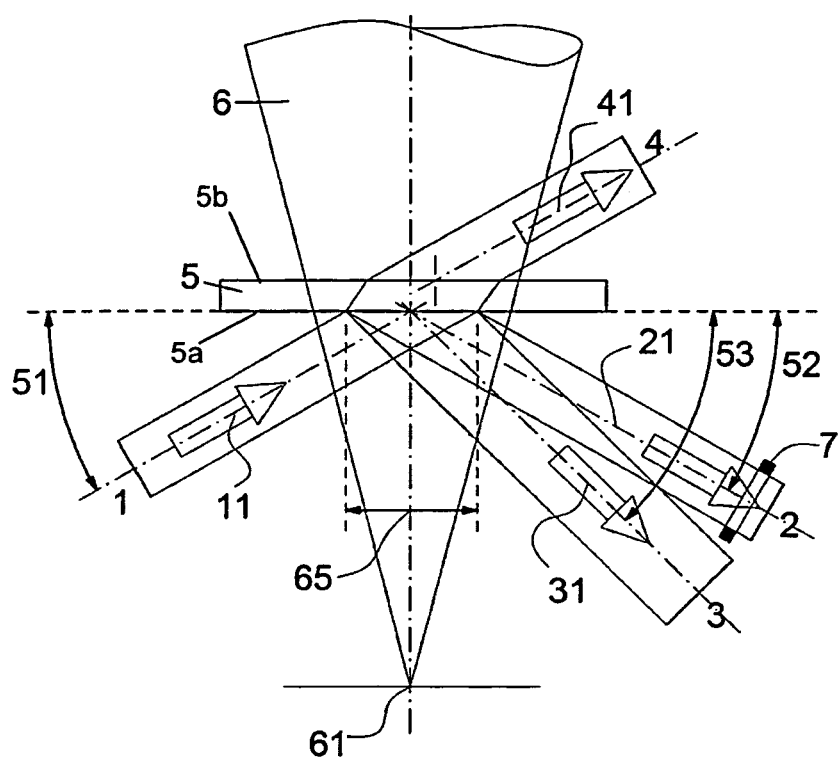
FIG. 1: schematic diagram of a device in accordance with the invention for the monitoring of a protective window.
Figure 6:
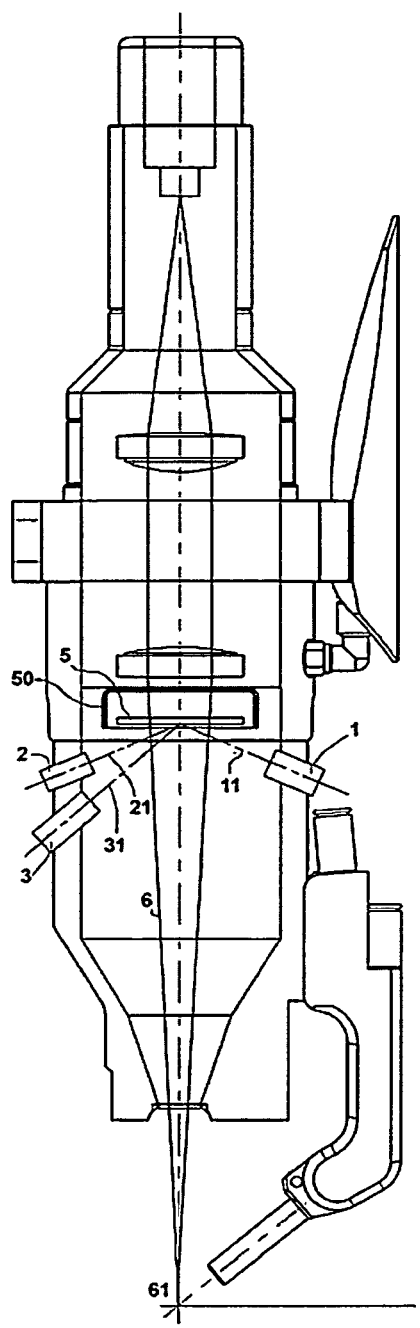
FIG. 6: cross-section through a processing head of a device for laser material processing with a protective window and a monitoring device in accordance with the invention.

To implement the method in accordance with the invention, a monitoring device is used, as shown schematically in FIG. 1. This monitoring device is provided for incorporation into the processing head of a device for laser material processing. Such a processing head is shown in FIG. 6.

The processing head emits a process laser beam 6 through a protecting, optically transparent window 5, which protects the other optical components in the processing head against process-caused spatters 55. The protective window 5 is appropriately provided with an antireflective (AR) coating. The process laser beam 6 is focused in a focal point 61 (tool center point, TCP) on the surface of a specimen to be processed.

The monitoring device shown in FIG. 1 comprises a light source 1, for example, a light-emitting diode or a laser diode, that irradiates a preferably collimated measurement beam 11 onto a central area 65 of the optical surface 5a of the protective window 5, facing the process, under an angle of incidence 51. The beam 21 reflected from the optical surface 5a of the protective window 5, under the angle of reflection 52 corresponding to the angle of incidence 51, is conducted through an aperture stop 7 with preferably the same diameter as the collimated beam 11 onto a light-sensitive detector 2. The scattered radiation, scattered diffusely from the optical surface 5a of the protective window 5 in the impact area 65 of the measurement beam 11, is detected with a second detector 3. The scattering angle 53 is thereby selected to be appropriately different from the angle of reflection 52 of the reflected radiation 21. The intensity of the scattered radiation is dependent on the degree of contamination of the protective window 5 and is especially influenced by any material spatters that are located on the optical surface 5a and have perhaps already been burned in there.

Alternatively and preferably, the intensity of the beam 41 of the measurement beam 11 transmitted by the protective window 5 is detected simultaneously by means of a third detector 4 located in the interior of the processing head (seen from the outside, behind the protective window 5). Preferably, the detectors 2, 3, 4, are selectively sensitive for the wavelength of the measurement beam, which is appropriately in the visible spectral range.

The selected angle of incidence 51 can be smaller or larger or exactly 30° and is primarily oriented according to the available space in the processing head. The angle of reflection 52 corresponding to this has the same magnitude as the angle of incidence 51. The scattering angle 53 is selected either smaller or larger than the angle of reflection 52. If it is selected to be the same magnitude as the angle of reflection 52, then the second detector is placed, staggered laterally, next to the first detector 2, so that the detectors 2 and 3, spatially separated from one another, always form the same impact surface 65 of the radiation 11 on the protective window 5.

Alternatively, additional detectors for the detection of the scattering radiation can be placed under different scattering angles, whose output signals are then appropriately added up and scaled correspondingly.

Figure 3:
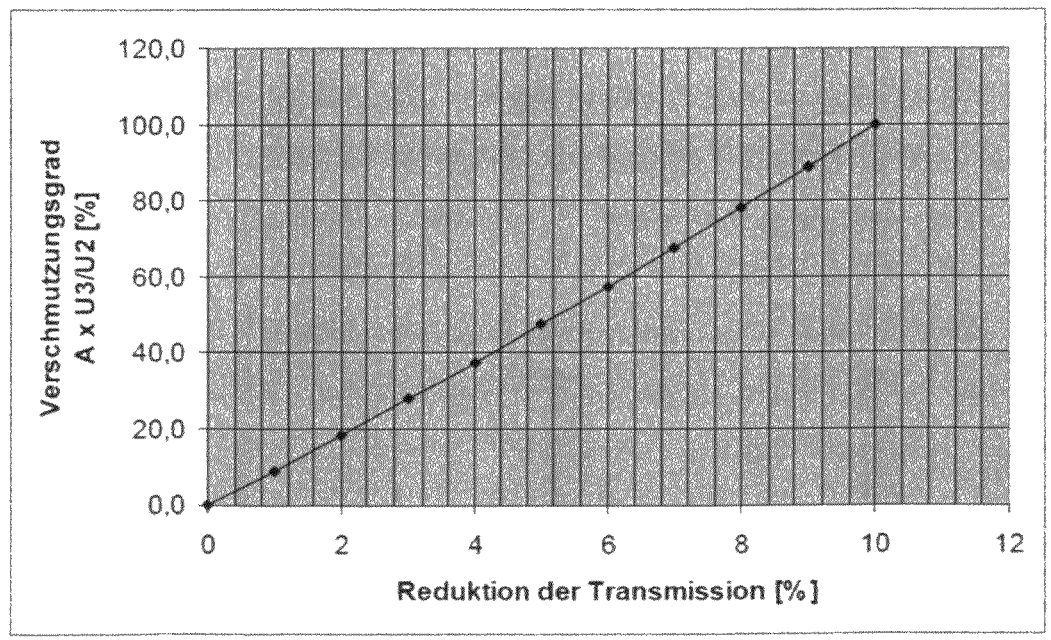
FIG. 3: relationship between the measured degree of contamination and the reduction of the optical transmission of the protective window of FIG. 1 as a result of the contamination.

For the determination of the degree of contamination of the protective window 5, the ratio of the output signals of the detectors 3 and 2 and/or the detectors 3 and 4 and/or the detector 3 is formed with the sum of the detectors 2 and 4 and compared to a pre-established switching threshold. As soon as contamination is present, the output signals of the detectors 2 and 4 become smaller and the output signal of the detector 3 becomes larger, compared to a protective window 5 that is not contaminated. Since the use of the detector 4 is dependent on the available space in the processing head, the ratio formation of the signals of the detectors 3 and 2 are the preferred evaluation method, which has all the advantages of the method in accordance with the invention. An idealized course of the degree of contamination measurement in accordance with the preferred evaluation method is shown in FIG. 3.

For the detection of the degree of contamination, the formation of the ratio of the signals of detector 3 and the sum of the signals of detectors 2 and 3 is also particularly suitable. The sum of the signals of detectors 2 and 3 basically represents a measure for the output of the measurement beam 11. However, the scattered radiation, scattered by any material spatters onto the optical surface 5a of the protective window 5, can be detected only incompletely because of practical and economic reasons, so that the measured signal becomes slightly nonlinear with the degree of contamination, but remains nevertheless monotonous.

Figure 5:
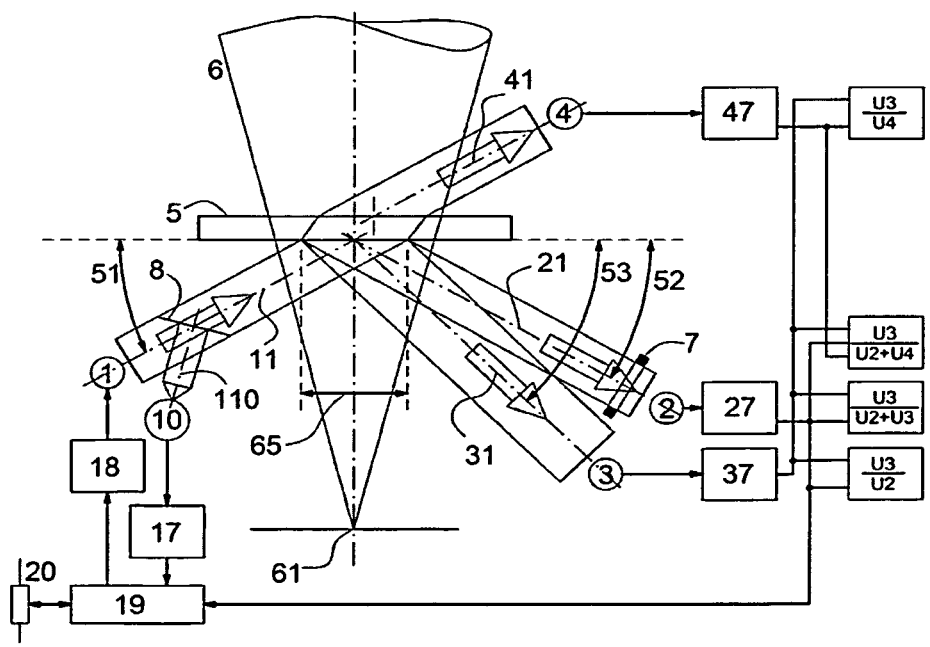
FIG. 5: schematic diagram of preferable expanded signal processing methods in accordance with the invention.

A mostly comparable possibility of the evaluation of the detector signals for the determination of the degree of contamination is given by the formation of a ratio between the signal of detector 3 and the momentary output of the measurement beam 11 emitted by the light source 1. This method, however, assumes that the output of the measurement beam is measured, via a monitor-photodiode 10, from the partial beam 110, which is reflected out from the measurement beam 11 via a partly transparent mirror 8, as shown in FIG. 5.

In the case that a monitor-photodiode 10 is used for the measurement of the momentary transmitting power, it is particularly advantageous if the output of the measurement beam 11 is regulated with the aid of the signal of detector 2 as the ACTUAL value, via a regulation 19. The output of the light source 1 is thereby subsequently always regulated to remain constant via the regulation 19 in such a way that the output signal of the detector 2 remains constant. The SET value 20 of the output of the light source 1 is hereby manually set. In the normal case (without contamination), this procedure ensures a constant output power of the light source 1, which is not constant in the case of a contamination. At the same time, with a replacement of the protective window 5, an adaptation to the optical characteristics of a new protective screen automatically takes place, which, for example, can come from another production batch or even from another supplier. Then if the contamination progresses, the signal of detector 2 would (as described above) become smaller, but the regulation 19 in this embodiment example would keep the level of the reflected radiation 21 constant. In accordance with the contamination-caused signal loss, the output power of the light source 1 is thereby increased, so that the signal of detector 3 (scattered radiation) rises proportionally with the contamination.

In the case that protective window 5 experiences a breakage, the signal of detector 2 becomes zero, which is in the denominator of the evaluation signal in the evaluation. In this way, the evaluation signal is undefined and leads to an electronically easily recognizable state. Furthermore, the comparison of the signal of detector 2 with a pre-established switching threshold also leads to the reliable detection of a breakage of the protective window 5. In addition, if a breakage has occurred, the transmission signal of detector 4 becomes larger than in the starting situation with a protective window that is not contaminated and intact and can also be used for the detection of a breakage.

Figure 2:
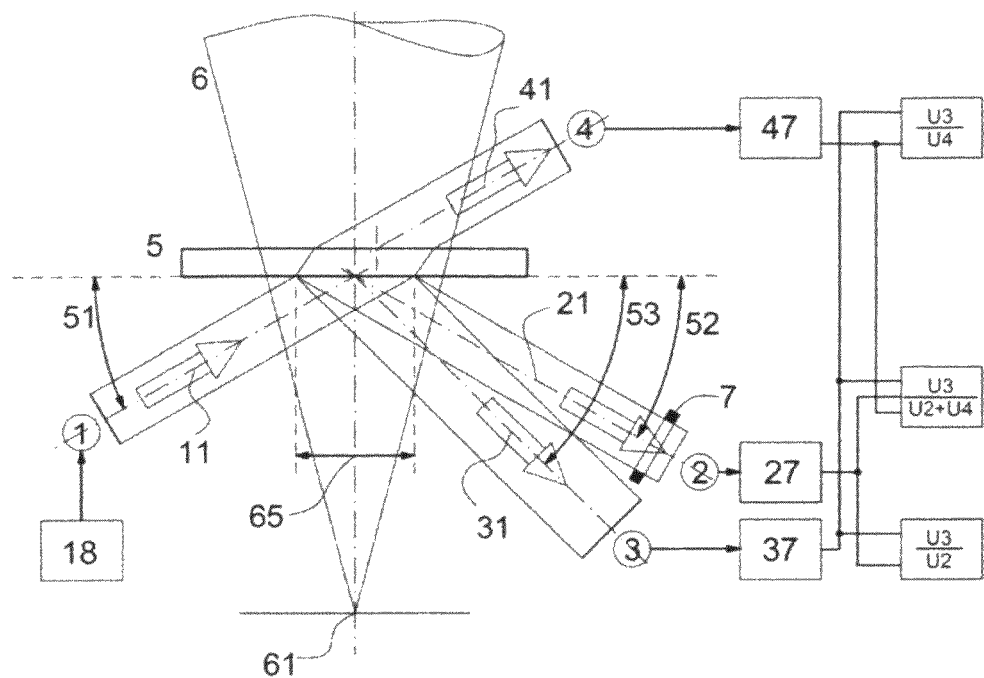
FIG. 2: schematic diagram of preferred signal processing methods in accordance with the invention.

FIG. 2 shows a driver 18 of the light source 1, which is preferably pulsed with a switching frequency F. Detector amplifiers 17, 27, 37, and 47 work synchronously in this embodiment example with the switching frequency F of the light source 1. In this way, a high operating reliability and a reliable suppression of daylight and other disturbing light and single sources are ensured.

The (not depicted) use of optical band pass filters, which are coordinated with the wavelength of the measurement beam 11, is also appropriate for the improvement of the sensitivity of the measurement.

Figure 4:
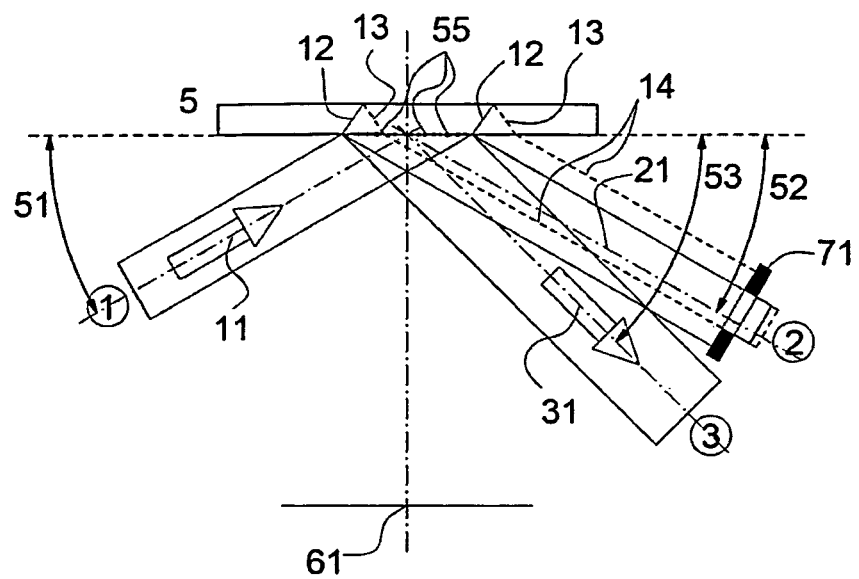
FIG. 4: schematic diagram of a beam path of a monitoring device in accordance with the invention, using the example of a protective window and the radiation of the measurement beam, using the beam refracted at the surface of the protective window, and the radiation reflected on the protective window, and the staggered exiting radiation, from the protective window.

FIG. 4 also shows the radiation 12, which is refracted in the protective window 5 and which is reflected, internally, to the upper surface of the protective window as radiation 13 (shown as a broken line) and is subsequently, again refracted at the lower surface of the protective window, as radiation 14 (broken line), exiting in a staggered manner (relative to the reflected radiation 21). This additional beam path shows that with favorable angles of incidence 51, a sufficiently large partial beam 12 of the radiation 11 is coupled into the protective window, so that its output through the burned-in material spatters 55 is reduced, so that with exiting, after the internal reflection as a partial beam 13, it is again modulated in output by the burned-in spatters 55. In this case, the aperture stop 7 sits on the new position which is marked by 71 in FIG. 4, where it allows only the intersection of beams 21 and 14 to pass through onto detector 2. In this case, the sensitivity of the measurement is improved.

The use of the monitoring device in accordance with the invention in a processing head according to FIG. 6 has the advantage that the components of the monitoring device can be firmly mounted in the lower part of the processing head in a well-protected manner, whereas the protective screen 5 is incorporated into a provided drawer 50 that can be readily replaced.

The monitoring device in accordance with the invention in FIGS. 1 and 4 can be used with limitations on the sensitivity and after nonessential technical adaptations, also with a non-collimated light source 1 with an easily divergent radiation 11.

The arrangement in accordance with the invention in FIGS. 1 and 4 can also be used not only for the monitoring of the contamination of protective window, but rather also for other optical components, such as for mirror surfaces or lenses, wherein the detection of the transmission radiation 41 with the detector 4 can be omitted with non-transmissive optical components such as mirrors.

Also advantageous is the fact that only one monitoring device in accordance with the invention is needed to monitor the optical component. From DE19839930 and DE20314918, it is, for example, known that for a reliable monitoring, several monitoring devices placed on the circumference of the optical component are needed.

Figure 7:
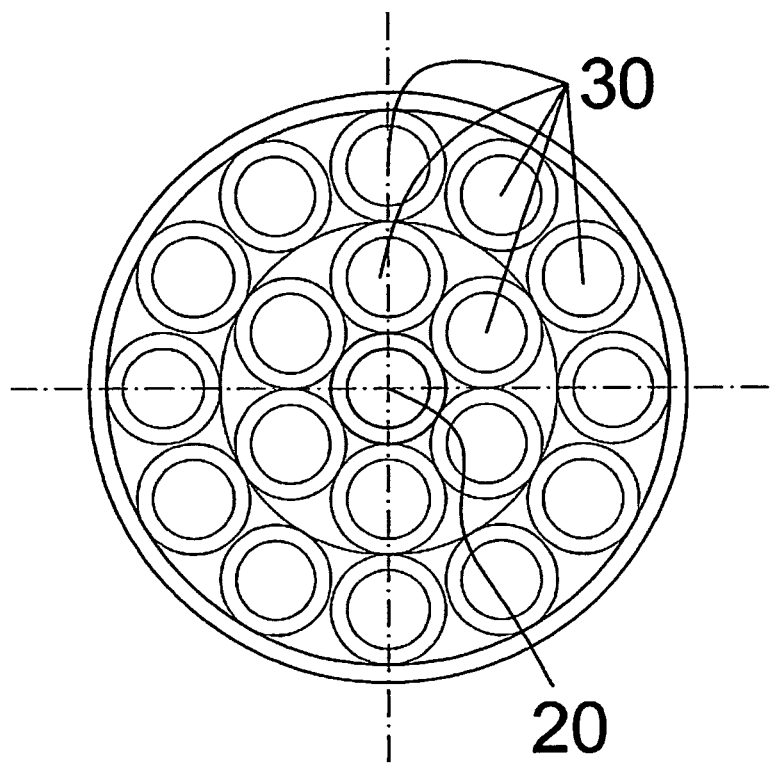
FIG. 7: schematic representation of the structure of an optical fiber bundle for the detection of the reflected radiation and the scattered radiation in accordance with the method according to the invention.

Both the light source 1 and also detectors 2, 3, 4 can be mounted as discrete components or via optical fibers in the needed position in or on the processing head. Detectors 2 and 3 can be designed in a particularly practical manner as optical fiber bundles, as shown in FIG. 7, wherein the fibers 20 and 30, which are shown with a fiber core and jacket, can also have different diameters.

A comparable coaxial arrangement of detectors 2 and 3 also allows, in a particularly practical manner, an implementation with a perforated mirror and two discrete detectors (without figure).

Instead of the proposed light-sensitive detectors 2 and 3, it is also possible to use matrix detectors (CCD-camera chips) or XY-position-sensitive detectors (PSD) without imaging optics for the detection of the shift of the center of light distribution in the reflected beams (total sum of the intensities of beams 21, 31, and 14) (without figure). The highest radiation density is given by the combination of beams 21 and 14 by the total sum of their intensities. In order to detect a shift with a minimum detector area, it must be located radially (spatially) staggered from detector 2 in the direction of detector 3.

In addition, the monitoring device from FIG. 4 can also be used for the selective detection of the contamination on the inner side 5b of the protective window 5 found in the processing head, provided that the optical side 5a remains, depending on the process, clean. In this case, the information regarding the degree of contamination of the inner side 5b is found in the partial beam bundle 14, so that for a better detection of the contamination, the beams 12 and 14 are separated as much as possible, in that the diameter of the measurement beam 11 is selected in a manner corresponding to or at least on the order of magnitude of the thickness of the protective window 5.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method for detection and monitoring of contamination of an optical component in a device for laser material processing, which emits a process laser beam through or onto the optical component, the method comprising the following steps:

projecting a measurement beam, emitted by a light source onto an optical surface of the optical component, whereby the measurement beam is collimated and has a predetermined diameter and strikes the optical surface of the optical component in collimated form under an angle of incidence, and thereby generates a collimated reflection beam which is reflected from the optical surface of the optical component under an angle of reflection corresponding to the angle of incidence and having the same diameter as the predetermined diameter of the measurement beam;

feeding the reflection beam through an aperture stop having the same diameter as the collimated measurement beam and to a first light-sensitive detector;

recording the intensity of said reflection beam reflected from the optical surface of the optical component and fed through the aperture stop with the first light-sensitive detector;

recording an intensity of scattered radiation of the beam, using a second light-sensitive detector whereby the scattered radiation is scattered diffusely by the optical surface of the optical component under a scattering angle; and determining the degree of contamination of the optical component from the recorded intensities of the reflected beam and the scattered radiation.

2. Method according to claim 1, wherein intensity of a transmission beam transmitted through the optical component is recorded by a third light-sensitive detector.

3. Method according to claim 1, wherein the measurement beam emitted by the light source impacts in a central area onto the optical surface of the optical component.

4. Method according to claim 1, wherein at least one of the first and second detectors is wavelength-selectively light sensitive with regard to the wavelength of the measurement beam.

5. Method according to claim 1, wherein the magnitude of the angle of incidence is equal to the magnitude of the angle of reflection.

6. Method according to claim 1, wherein the angle of reflection and the scattering angle are different.

7. Method according to claim 1, wherein power of the measurement beam emitted by the light source is recorded via a monitor diode, and the degree of the contamination of the optical component is determined from the recorded intensity of the scattered radiation and the power of the measurement beam.

8. Method according to claim 7, wherein the output of the measurement beam emitted by the light source is subsequently regulated via a regulation device in such a way that the signal of the reflected beam detected by the first detector is maintained constant, independent of the degree of the contamination of the optical component.

9. Method according to claim 1, wherein the optical component is a protective window, a lens, or a mirror.

10. The method of claim 1, wherein the measurement beam strikes the optical surface at an angle of about 30 degrees.

11. A device for detection and monitoring of contamination of an optical component in a device for laser material processing, which emits a process laser beam through or onto the optical component, the device comprising:
a light source configured to emit a collimated measurement beam and to project the measurement beam in collimated form and under an angle of incidence onto an optical surface of the optical component, whereby the collimated measurement beam has a predetermined diameter and enters the optical surface of the optical component with the predetermined diameter;
a first light-sensitive detector;
an aperture stop configured to pass a reflection beam, reflected under an angle of reflection from the optical surface of the optical component in collimated form and having a diameter equal to the predetermined diameter of the measurement beam, whereby the diameter of the aperture stop is equal to the diameter of the collimated measurement beam and the reflection beam passes through the aperture stop and onto the first light-sensitive detector, to thereby enable a recording of an intensity of the reflection beam;
a second light-sensitive detector configured to record an intensity of scattered radiation from the beam, the scattered radiation being scattered diffusely from the optical surface of the optical component under a scattering angle; and
an evaluation device configured to measure an extent of contamination of the optical component using the recorded intensities of the reflection beam and the scattered radiation.

12. Monitoring device according to claim 11, wherein the optical component is a protective window, a lens, or a mirror.

13. A method for detecting an extent of contamination of an optical component, comprising:
projecting a collimated measurement beam emitted from a light source and having a predetermined diameter under an angle of incidence in collimated form onto an optical surface of the optical component, thereby generating a reflection beam being reflected in collimated form from the optical surface of the optical component under an angle of reflection corresponding to the angle of incidence of the collimated measurement beam and having a diameter equal to the predetermined diameter of the collimated measurement beam;
feeding the collimated reflection beam through an aperture stop having a diameter equal to the diameter of the collimated measurement beam;
detecting a reflected intensity of the reflection beam, using a first light sensitive detector, after the reflection beam is fed through the aperture stop;
outputting a signal, from the first light sensitive detector, corresponding to the detected reflected intensity of the reflection beam;
detecting a scattered intensity of the beam, substantially simultaneously with respect to detection of the intensity of the reflection beam by the first light sensitive detector, using a second light sensitive detector, after the beam has been scattered diffusely by the optical surface of the optical component;
outputting a signal, from the second light sensitive detector, corresponding to the detected scattered intensity; and
determining an extent of contamination of the optical component using the outputted reflected and scattered intensities.

14. The method of claim 13, wherein an intensity of transmission of a beam through the optical component is recorded by a third light-sensitive detector.

15. The method of claim 13, wherein at least one of the first and second light sensitive detectors is wavelength-selectively light sensitive with regard to the wavelength of the measurement beam.

16. The method of claim 13, wherein the magnitude of the angle of incidence is equal to the magnitude of the angle of reflection.

17. The method of claim 13, wherein the angle of reflection and the scattering angle are different.

18. The method of claim 13, wherein a power level of the measurement beam emitted by the light source is recorded, and the degree of the contamination of the optical component is further determined using the power of the measurement beam.

19. The method of claim 13, wherein the output of the measurement beam emitted by the light source is regulated via a regulation device in such a way that the signal of the reflected beam detected by the first detector is maintained constant, independent of the degree of the contamination of the component.

20. The method of claim 13, wherein the measurement beam strikes the optical surface at an angle substantially less than 90 degrees.

* * * * *